United States Patent [19]

Hales

[11] 4,108,975

[45] Aug. 22, 1978

[54] RADIOIMMUNOASSAY SYSTEM

[75] Inventor: Richard Harold Hales, West Jordan, Utah

[73] Assignee: Becton, Dickinson and Company, Rutherford, N.J.

[21] Appl. No.: 774,277

[22] Filed: Mar. 4, 1977

[51] Int. Cl.$^2$ .................... G01N 33/16; A61K 43/00; B01J 1/22

[52] U.S. Cl. ..................... 424/1; 23/230 B; 23/230.6; 424/12

[58] Field of Search ............................ 424/1, 1.5, 12; 23/230 B, 230.6

[56] References Cited

U.S. PATENT DOCUMENTS

| | | | |
|---|---|---|---|
| 3,505,785 | 4/1970 | Kirkland | 55/67 |
| 3,788,948 | 1/1974 | Kagedal et al. | 424/1 X |
| 3,796,634 | 3/1974 | Haynes et al. | 195/63 |
| 3,896,217 | 7/1975 | Johnson | 424/1 |
| 3,979,184 | 9/1976 | Giaever | 23/230 B X |
| 3,979,509 | 9/1976 | Giaever | 23/230 B X |

*Primary Examiner*—Richard E. Schafer
*Assistant Examiner*—Christine M. Nucker

*Attorney, Agent, or Firm*—Mario A. Martella

[57] ABSTRACT

An improved radioimmunoassey procedure involves the use of an improved reusable immunoadsorbent through which a sample of an antigen and radioactive labelled antigen is flowed to form a bound and unbound fraction. The bound fraction is releasably coupled to the immunoadsorbent which includes a solid particulate substrate to which antibodies, specific to the antigen, are covalently bonded by reaction between the carboxyl or amine group of the antibody and a group such as an acyl azide, carbonate, thiocarbonate, polythiol, isocyanate, epoxide and chlorothioformate group, for example, reacted on the substrate. The substrate includes a porous refractory material having at least one polymeric material bonded thereto as a barrier and to which is linked one of the above groups for reaction with the carboxyl or amine group of the antibody. The antigen bound to the immunoadsorbent is stoichiometrically released by an eluting solvent and the immunoadsorbent is reused. Concentration of the antigen is determined with reference to one of the bound or unbound fractions, or both.

17 Claims, No Drawings

RADIOIMMUNOASSAY SYSTEM

RELATED APPLICATIONS

Reference is made to Applications Ser. No. 565,848, now U.S. Pat. No. 4,059,685, and 565,850, now U.S. Pat. No. 4,009,005 each filed Apr. 7, 1975; and Ser. No. 774,390 filed of even date herewith, each assigned to the same assignee. Reference is also made to U.S. Pat. No. 3,896,217 issued on July 22, 1975.

BACKGROUND OF THE INVENTION

This invention relates to radioimmunoassay and more particularly to an improved radioimmunoassay procedure using an improved immunoadsorbent which is used for repeated assays.

STATE OF THE ART

Radioimmunoassay is an analytical technique which depends upon the competition (affinity) of antigen for antigen-binding sites on antibody molecules. In practice, standard curves are constructed from data gathered from a plurality of samples each containing (a) the same known concentration of labelled antigen, and (b) various, but known, concentrations of unlabelled antigen. Antigens are labelled with a radioactive isotope tracer. The mixture is incubated in contact with an antibody, the free antigen is separated from the antibody and the antigen bound thereto, and then, by use of a suitable detector, such as a gamma or beta radiation detector, the percent of either the bound or free labelled antigen or both is determined. This procedure is repeated for a number of samples containing various known concentrations of unlabelled antigens and the results plotted. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In actual analysis, the sample in which the concentration of antigen is to be determined is mixed with a known amount of tracer antigen. Tracer antigen is the same antigen known to be in the sample but which has been labelled with a suitable radioactive isotope. The sample with tracer is then incubated in contact with the antibody. Thereafter, it may be counted in a suitable detector which counts the free antigen remaining in the sample. The antigen bound to the antibody or immunoadsorbent may also be similarly counted. Then, from the standard curve, the concentration of antigen in the original sample is determined. Afterwards, the antibody or immunoadsorbent mass is discarded.

In order to detect the percentage of antigen that is bound to the antibody (bound antigen) and/or the percentage that remains free or unbound it is necessary first to separate the sample into a fraction containing bound antigen and one containing only free antigen. One common method for doing this is to add a dextran coated charcoal to the mixture. The dextran permits the unbound antigen, of lower molecular weight than the bound antigen, to pass through the dextran and the charcoal adsorbs the free antigen. The charcoal with adsorbed free antigen is then separated from the antibody (and bound antigen) by centrifugation.

Another known procedure is to add to the mixture another antibody which selectively precipitates the first antibody (with the bound antigen) thus leaving in solution only free antigen. Classification into appropriate free and bound fractions is then effected by separating the precipitate from the supernate by centrifugation or other suitable means. Some workers have resorted to the technique of binding the antibody to the inner walls of a plastic vessel, filling the vessel with the antigen bearing sample, allowing it to stand for an incubation period that typically ranges from 15 minutes to 72 hours and then separating free antigen from bound antigen by draining and rinsing the vessel leaving therein only the antibody and bound antigen. A more recently developed technique is to prepare the immunoadsorbent by binding the antibodies onto an insoluble cross-linked dextran. The immunoadsorbent and antigen bearing sample are incubated and then the dextran with bound antigen is separated from the solution by suitable means.

In all of the foregoing procedures, the percentage of labelled antigen in either or both the bound or free fractions is determined and the standard curve used to determine the antigen concentration. Thereafter, the immunoadsorbent is discarded.

Although the foregoing radioimmunoassay techniques have proven to be valuable tools and have gained widespread acceptance, they are still not all that are to be desired because the antibody (immunoadsorbent) is consumed with each analysis and hence must be discarded. Moreover, prior practice is batch type and the several reagents are added to the antibody in test tubes in which the separate steps, such as incubation, rinsing and the like, are performed, thus resulting in a slow and costly operation.

The above-identified applications and patent describe a substantial improvement in immunoassay procedures in that the same immunoadsorbent may be used repeatedly for many assays by releasing from the immunoadsorbent the antigen which is bound to the antibody mass, the latter immobilized on the substrate; i.e. selectively and stoichiometrically releasing all of the antigen on the immunoadsorbent after the assay is completed. The present invention relates to an improvement over the system above described.

DESCRIPTION OF THE PRIOR ART

It is known from the literature that antibodies may be isolated by use of immunologic adsorbents, the technique being useful for isolation and purification of antibodies rather than quantitative determination thereof, see Campbell et al, *Proc. Nat'l. Acad. Sci. U.S.* 37 (1951) 575.

The use of an antibody coupled to an insoluble polymer for extracting specific antigens for purposes of isolating and purifying the same is described in Weetall et al, *Biochem. Biophys. Acta.* 107 (1965) 150–152.

Porous glass has been described as a substrate for immobilizing enzymes, see Weetall, *Biochem. Biophys. Acta.* 212 (1970) 1–7. There, glass was treated with gamma aminopropyltriethoxysilane and the isothiocyanate derivative was prepared by treatment with thiophosgene. The enzyme was coupled to the isothiocyanate derivative. Also described is the preparation of an arylamine derivative by the reaction of alkylamine glass with P-nitrobenzoyl chloride followed by use of sodium dithionate to reduce the nitro groups. The arylamine glass was then diazotized and the enzyme coupled thereto.

Weetall, in Biochem. J. (1970) 117, 257–261 also describes the use of antibodies bound to porous glass through a silane coupling agent, the immunoadsorbent being used to isolate and purify specific antigens. The data given, however, shows that the reused column, in which the antigen was eluted from the immobilized antibody immunoadsorbent was quite erratic in performance since the recovery of released antigen varied from 74% to 100%. See also U.S. Pat. No. 3,652,761 of Mar. 28, 1972. While useful as an isolation system, the described system has considerable objections from the standpoint of a useable tool in quantitative analysis in which there must be substantially stoichiometric release of the antigen.

U.S. Pat. No. 3,555,143 of Jan. 12, 1971, relates to radioimmunoassay procedures in which an immobilized immunoadsorbent is used only once and then discarded. The immunoadsorbent is a dextran (Sephadex G 25, superfine) cross-linked with glycerine ether bridges and substituted with p-nitrophenoxyhydroxy-propyl groups. The nitro groups are reduced to amine groups using sodium dithionite. The Sephadex substituted with p-amino-phenoxy-hydroxy-propyl groups was then treated with thiophosgene to form Sephadex substituted with p-isothiocyanatephenoxy-hydroxy-propyl groups, the antibody being bound to the latter substituted product.

A reaction widely used to insolubilize a protein involves a covalent binding of the protein to a cyanogen bromide activated cellulose matrix. The mechanism of such activation is set forth in Bartling et al, *Biotechnology and Bioengineering*, Vol XIV (1972) 1039–1044.

U.S. Pat. Nos. 3,502,888 of July 13, 1971; 3,639,559 of Feb. 1, 1972, and 3,720,760 of Mar. 13, 1972 are also of interest.

Where an immobilized immunoadsorbent is to be used only once and discarded, the long term properties of the substrate are not of major consequence. Thus, materials such as Sephadex (dextran) or Sepharose (beaded agarose product) operate satisfactorily as substrates for antibodies bound thereto as described in U.S. Pat. No. 3,555,143, supra. Where the immunoadsorbent is to be used repeatedly, as described in the above-identified applications and U.S. Pat. No. 3,896,217, certain problems arise.

One of the objections is the tendency of Sephadex and Sepharose type products to dehydrate, that is, the gel collapses and packs to such an extent that flow through the mass is substantially impeded and the availability of antibody for binding antigen is altered, thus affecting the reproducibility and stability of the immunoadsorbent for repeated use.

Glass and other solid inorganic materials offer a desirable alternative because they can be formed into beads to provide better flow and easier packing into a column type arrangement. Such materials do not collapse and are not subject to dehydration during periods of extended use. While a desirable alternate, glass type products also suffer from disadvantages. One of the problems is obtaining a sufficient binding of the antibody to the substrate. Either an insufficient initial binding takes place to provide the activity needed for a quantitative analysis tool, or the activity changes over the life of the immunoadsorbent by undesirable release of antibodies.

Where the glass is highly porous, as that used by the Weetall references cited, there is so much active glass surface area that ample binding of the antibody takes place but nonspecific binding of the antigen also takes place. Thus, the antigen bound to the glass is not released completely. That is, rather than having a stoichiometric release, for each use thereof, as is needed for quantitative analysis, the release characteristics are variable and unpredictable. This is confirmed by the Weetall data. Since such glass is usually 96% air or void space, there is considerable active surface area of the glass, not occupied by antibody which serves as an antigen binding site.

Another difficulty with highly porous glass products is that there are multiple crevices in the pores which result in trapping in the crevices and slow release because of the slow diffusion in the crevices. Where a fast response is needed, as for example in automated equipment of the type described in Ser. No. 565,850, the diffusion of the reactants is a rate limiting step and, as is well known, diffusion may be a relatively slow process. Thus, even if not bound to the substrate, the diffusion of the antigen is relatively slow and thus, for the purpose of rapid automated assay equipment, the antigen is effectively bound rather than being rapidly and stoichiometrically released.

Superficially porous supports are known for use in chromatography, see for example U.S. Pat. No. 3,505,785 of Apr. 14, 1970, which describes a product commercially available from E. I. du Pont de Nemours and Co. under the trademark "Zipax". These support beads for use as chromatographic column packing consists of a plurality of discrete macroparticles with impervious cores and having irreversibly joined thereto a coating of a series of sequentially adsorbed monolayers of like colloidal microparticles. Thus, spherical glass microbeads of about 30 microns diameter include an outer porous surface crust which is about one micron thick. Such as material, if used as a substrate offers substantial surface area for the desired activity, but the substrate must be properly prepared to assure the proper quick response as well as stoichiometric release.

The prior art describes various methods for covalent attachment of enzymes to water insoluble carriers, see for example "*Immobilized Enzymes for Industrial Reactors*" by Ralph A. Messing, Academic Press, New York, N.Y., 1975. While these prior art teachings may be useful, the problems of radioimmunoassay using a regenerated immunoadsorbent are not solved by these teachings. In large measure the nature of the substrate is important in a flow-through system of the type to which this invention relates.

More specifically, the amount of activity of the immunoadsorbent and the stoichiometric release of antigen are critical, thus raising unique problems since the release must be essentially complete for accuracy of subsequent assays. If the eluting solvent adversely affects the material bound to the solid substrate, accuracy is affected adversely. Retention of antigen on the substrate is also a possible problem. Thus, merely because certain chemistry is described in the prior art with reference to enzyme or protein reaction, it does not assure that the same or substantially the same chemistry will be operative in the case of antibodies to be used in an immunoadsorbent intended for use and reuse in radioimmunoassay.

Thus, the provision of a reusable immunoadsorbent and which stoichiometrically releases the antigen for each assay is quite desirable. Where that immunoadsorbent is also substantially free of dehydration and packs such that the flow quality through the mass is of desirable character over the useful life of the immunoadsorbent, a substantially improved reusable immobilized immunoadsorbent is provided. Such a material is described in Ser. No. 565,848 and the present invention represents an improvement thereover.

In accordance with this invention an improved radioimmunoassay procedure is provided in which an improved immobilized immunoadsorbent is used in a flow through system in which the immunoadsorbent is reused.

The sample, usually containing an unknown amount of antigen and a known amount of radioactive labelled antigen is flowed through an immobilized immunoadsorbent supported in a chamber which may be of the type described in Ser. No. 565,848, supra. During flow through the immunoadsorbent, a portion of the sample (antigen and labelled antigen) is bound to the antibody which is covalently coupled on the immunoadsorbent, thus forming a bound and free fraction. The bound fraction is stoichiometrically released from the immunoadsorbent by flowing an eluting solvent therethrough. Quantitative determination of the antigen, in nano- and pico-gram quantities may be made by monitoring the radioactivity of the released or bound fraction or both, by the use of standard curves. The procedure for generating standard curves is well known in the art. Automated equipment for carrying out the above process is described in Ser. No. 565,850.

The immunoadsorbent includes a solid particulate substrate having functional groups such as acyl azide, chlorothioformate, epoxide, carbonate, thiocarbonate, isocyanate, cyanuric chloride, polyazide, polychlorothioformate, polyepoxide, polycarbonate, polyisocyanate, polycyanuric chloride, polyimidocarbonate, polythiol, and polyaldehyde groups reacted thereon and capable of reacting with the amine or carboxyl groups on the antibody to bind or immobilize the antibody by a covalent bond.

The substrate is preferably a porous refractory material in particulate form having a relatively high surface area and having a polymeric material bonded thereto acting as a barrier, to which is linked one of the above mentioned groups for reaction with the reactive groups on the antibody.

DETAILED DESCRIPTION OF THE INVENTION

The improved method of the present invention using the improved immunoadsorbent herein described may be used in a radioimmunoassay procedure in which quantitative determinations may be made of the following: estriol, digoxin, digitoxin, testosterone, estradiol, aldosterone, progesterone, cortisol, 11-desoxycortiosterone, 11-desoxycortisol, thyroid hormones such as thyroxin ($T_4$) triiodothyronine ($T_3$), polypeptides such as angiotensin, TSH (thyroid stimulating hormone), ACTH, GH (growth hormone), HP (human placentolactogen), parathormone, calcitonin, insulin, glucagen, polypeptide proteins such as CEA (Carcino embrionic antigen), alphafetoprotein, interferon, viruses such as Australia antigen, vitamins such as D and $B_{12}$ folic acid and drugs such as dilantin and barbiturates, to mention only a few.

The antisera for the above antigens are known, as are the labelled antigens, available in the form of radioactive isotope labelled materials, usually in the form of the $I^{125}$ isotope or $H^3$ isotope.

The immobilized immunoadsorbent includes a substrate with which the antibodies are relatively permanently associated. In use, an unlabelled antigen sample with a known concentration of labelled antigen is brought into contact with the immobilized immunoadsorbent disposed in a chamber holder. When brought into contact, a portion of the mixture of labelled antigen and unlabelled antigen binds to the specific antibody bound on the substrate. Thereafter, the unbound antigen or the bound antigen or both are counted and concentration of the unlabelled antigen is determined from standard data.

Thereafter, the immobilized immunoadsorbent is eluted with an appropriate aqueous solution containing solvents such as methyl alcohol, isopropyl alcohol or ethyl alcohol as well as dimethyl formamide to effect a stoichiometric release of the bound labelled and unlabelled antigen from the immobilized immunoadsorbent. The rinsing or eluting operation effectively regenerates the immunoadsorbent for reuse, and thereafter, the same immunoadsorbent may be used again, repeatedly, for assays of that antigen as to which the immobilized antibody is specific, with washings, as described between each use.

Since the antigen material is flowed into a chamber supporting the immunoadsorbent which is reused, the flow characteristic of the substrate should be such that contact is achieved between the supported antibodies and antigen mixture. Moreover, the substrate must be of such a type as not to interfere with release of the bound antigen while retaining the bound antibody. Reproducibility, stability and speed are some of the advantages of the improved method, and thus the substrate must be such that sufficient activity may be obtained in terms of bound antibody with available antigen binding sites. It is preferred, therefore, that the substrate be particulate, and spherical i.e. formed of a mass of discrete particles since this enhances the desirable flow-through character of not only the sample mixture of labelled and unlabelled antigen, but of the rinse or eluting medium as well.

Particulate materials capable of providing the needed antibody activity are known, e.g. Sephadex, Sepharose, porous glass and the like. Materials such as Sephadex and Sepharose are gel type materials and over periods of extended use, tend to dehydrate resulting in collapse with resulting packing which impedes the flow. Materials such as porous glass are so active that antigen is bound to the glass and not released.

Thus, an important aspect of this invention is the use of an immunoadsorbent which includes formation of a barrier coating over a particulate substrate, the barrier coating operating to provide, in effect, a mask which precludes the potentially active sites on the substrate from irreversibly binding the antigens. The barrier also functions as an immobilized component of the substrate to which the antibodies may be attached. Since assays are conducted in aqueous and non-aqueous solvents, the barrier coating is preferably insoluble and not adversely affected by the solvents and solutions used in the procedure. Water insoluble polymer materials such as dextran, polyolefins, carboxymethyl cellulose, cellulose or combinations thereof are preferred in accordance with this invention.

The substrate itself is preferably a particulate material resistant to dehydration and collapse. Rapid mass transfer at relatively high flow rates are a function of substrate geometry, and packing character in the chamber holder. A preferred substrate is a material having a controlled surface porosity, superficially porous refractory particles made up of discrete macroparticles with impervious non-porous cores, and having joined thereto a coating of a series of sequentially adsorbed monolayers of like inorganic microparticles.

The superficially porous refractory particle which forms the substrate for the immobilized immunoadsorbent includes a core in the form of a macroparticle which is an impervious non-porous core. The core is preferably spherical because this shape is preferred for packing purposes. The core, in the form of a sphere is of a diameter of between 5 and 500 microns in diameter and composed of glass, although it may be of sands, ceramics, and the like.

The cores are preferably of uniform size i.e. all within about 50% of the average diameter. Affixed to the core is a plurality of layers of microparticles which form an outer porous coating. The microparticles may range in size from 5 millimicrons to 1 micron, and the number of layers may be between 2 and 30. The micro-particles may be amorphous silica, alumina, thoria and the like.

As will be apparent, a substrate of material as described has a relatively high surface area due to the porous coating, but is relatively free of pores in the core material. For beads of an overall diameter of 30 microns, and a porous crust of one micron, a surface area of between 0.8 to 1.0 m$^2$/gram is obtained, with a packed bed density of 1.5g/cc. The regular geometry, the stability against dehydration and collapse, and the bulk renders the above material quite exceptional as a substrate. A typical such material is that available under the name "ZIPAX".

However, there is a tendency for such a material, if used in the form described as a substrate directly for the antibody material, to contain active sites which tend to bind the antigen mixture or a component thereof in a nonreleasable manner. This problem may be quite objectionable where the immobilized immunoadsorbent is reused, an important objective in this invention. Since the accuracy and speed of the assay is, in part, related to the ability of the antibody to bind the antigen and stoichiometrically to release the same when rinsed, any unreleased antigen adversely affects the accuracy of subsequent assay. While a background count could be taken, this is not entirely satisfactory since the retention-release phenomena tends to be non-uniform and non-predictable.

The tendency to bind in a non-releasable manner is substantially eliminated by the use of a barrier coating adhered to the substrate, which may be achieved in several ways.

The substrate is reacted with 3-aminopropyltriethoxysilane to form an aminoalkylsilane derivative in which the amino group is at the free end, i.e. a substrate-amine derivative. By treatment of the amine derivative, with thiophosgene, the amino groups are converted to isothiocyanate groups, i.e. an isothiocyanate derivative is formed.

The isothiocyanate derivative may be reacted with dextran which is activated by treatment with cyanogen bromide (reacting with the hydroxyl groups) to form an imidocarbonate on the dextran for conjugation with an antibody. This product is well known in Ser. No. 565,848 and forms no part of this invention. The product does offer a standard against which the performance of either system may be evalulated.

By this invention, the isothiocyanate derivative may be reacted with cellulose to form a hydroxyl deriative which may in turn be treated with a halogenated acid such as bromo acetic acid, chloro-acetic acid, 6-bromo hexanoic acid or 5-chlorovaleric acid to form a carboxyl derivative. The carboxyl derivative may be treated with thionyl chloride to form the acid chloride which is treated with sodium azide to form an acyl azide derivative to which the antibody is conjugated.

The isothiocyanate derivative may be reacted with carboxymethyl cellulose to form a carboxyl derivative followed by conversion to the acyl chloride and then to the acyl azide by treatment with sodium azide. The antibody may be conjugated, in either case by reaction of the amine group on the antibody and the acyl azide group on the substrate.

Rather than activate the dextran coated substrate formed from the isocyanate derivative, by treatment with cyanogen bromide, a toxic material which requires special precautions, activation for conjugation of the antibody may be achieved by a halogenated acid or succinic anhydride to form a carboxyl derivative followed by formation of the halide and the azide derivative, as previously disclosed. In this form of immunoadsorbent, the hydroxyl groups of the dextran coated substrate are reacted with one of chloracetic acid, bromoacetic acid, 5-clorovaleric and 6-bromohexanoic acid to form the carboxyl derivative followed by formation of the acyl chloride by use of thionyl chloride and conversion to acyl azide by sodium azide treatment. Where succinic anhydride is used, a carboxyl derivative is formed by a linkage through an ester group to the dextran, the carboxyl group then being converted to an azide by treatment with thionyl chloride and sodium azide.

The dextran coated substrate may be activated by treatment with ethyl chloroformate or carbonyl diimidazole to form a carbonate derivative, or with epichlorohydrin to form an epoxide derivative, with thiophosgene to form a chlorthioformate derivative, with thiocarbonyl diimidazole to form a thiocarbonate derivative and with toluene diisocyanate to form an isocyanate derivative. In each case the formed derivative is used to conjugate the antibody to the substrate.

Of the above, the dextran derivative activated by treatment with a halogenated acid, e.g. chloroacetic acid, to form the carboxyl derivative and converted to an acyl azide is preferred. In a typical procedure adopted from Michael et al, *J. Makromol. Chem.* 3, 200 (1949) for the preparation of carboxymethyl cellulose, dextran coated material, prepared from the isothiocyanate derivative is used as the starting product. Two grams are stirred for three hours at room temperature with 20 grams of chloroacetic acid in 38 ml of a 40% NaOH solution to form a carboxy derivative of the general structure [S-D]*—O—[CH$_2$]$_n$—COOH, wherein $n$ may equal 1 to 5. In the case chloro- or bromoacetic acid, $n$ is one. The product is filtered, washed with water and acetone and air dried.

*[S-D] signifies dextran coated substrate.

Approximately 0.5 gm of the carboxyl derivative is then refluxed for 30 minutes in four ml of thionyl chloride to form the acid chloride. After filtration and washing with acetone, the product is suspended in acetone and added in portions over a period of 30 minutes to five ml of stirred 50 mg/ml solution of sodium azide in water. The mixture is stirred for an additional 30 min., five ml of water are added, and the mixture stirred for one hour. The formed azide derivative is then filtered and air dried.

In the conjugation of the antibody, the salt precipitate from 0.1 ml of serum is dissolved in 0.8 ml of 0.1 M sodium bicarbonate solution and allowed to incubate with cold (unlabelled antigen for 30 min. This mixture is added to 300 mg. of the acyl azide activated dextran support and rotated at 4° C for three days. The antibody support is then washed with 0.5 M NaCl, 50 mM phosphate buffer (pH 5.5) and 0.1 M Tris buffer (pH 8.5) washes followed by a final wash with 10 ml of 0.05 M phosphate buffer, pH 7.5, containing 0.05 M sodium chloride and 0.5% bovine serum albumin and 0.02% sodium azide as a preservative. The resulting product is then resuspended in 10 ml of the last wash solution and stored at 4° C.

A series of standard curves were prepared using the above immobilized immunoadsorbent placed in a chamber as described in Ser. No. 565,848 and by use of the equipment described in Ser. No. 565,850. Standards of varying known concentrations ng (ml) from 0 to 16 were used with five sets of data generated, as follows:

TABLE I

| | Estriol Antibody and Standards | | | | | | | |
|---|---|---|---|---|---|---|---|---|
| Run | 0* | .25 | .5 | 1 | 2 | 4 | 8 | 16 |
| 1 | 60.3** | 53.1 | 49.1 | 41.3 | 30.3 | 20.7 | 12.2 | 8.4 |
| 2 | 59.1 | 52.3 | 49.2 | 40.4 | 29.8 | 20.0 | 12.5 | 8.6 |
| 3 | 57.9 | 51.2 | 47.2 | 39.7 | 28.3 | 19.7 | 11.9 | 7.8 |
| 4 | 58.5 | 51.8 | 49.0 | 40.4 | 28.8 | 19.3 | 11.4 | 7.5 |
| 5 | 59.4 | 51.6 | 47.7 | 39.6 | 28.9 | 20.0 | 12.1 | 6.8 |
| Mean | 59.04 | 52.0 | 48.4 | 40.3 | 29.2 | 19.9 | 12.0 | 7.82 |
| SD*** | .9099 | .731 | .923 | .683 | .811 | .513 | .409 | .723 |
| CV**** | 1.54 | 1.41 | 1.91 | 1.70 | 2.77 | 2.57 | 3.40 | 9.24 |

*Concentration of standard in ng/ml
**Expressed as percentage bound
***Standard deviation
****Coefficient of variation Same designations apply to all tables.

These data indicate good performance and good release following elution of the bound fraction.

In another approach, the substrate is reacted with vinyltrichlorosilane to form a vinyl coated derivative, [S]-CH=CH$_2$, which may then be treated several different ways. In one series, the vinyl coated derivative is treated with acrylic acid to form the polyacrylic acid coated derivative which may then be treated with thionyl chloride and sodium azide to form a polyazide derivative to which the antibody is conjugated.

The procedure involves refluxing 25 grams of the solid carrier (Zipaz) for two hours with 41 ml (50.96 gm) of vinyltrichlorosilane in 85 ml of isooctane while mechanically stirring. The product is the vinyl coated derivative, which is then filtered, washed with isooctane and acetone and either air dried or heated to 80° C in an oven for two hours. A 6.25 gram sample of the vinyl coated derivative is then refluxed for 2 hours in a mechanically stirred solution of 2.5 ml (2.66gm) of acrylic acid and 0.25 gm of benzoyl peroxide in 624 ml of acetonitrile to form a polyacrylic acid coated derivative which is then filtered and Soxhlet extracted for one day in each of acetonitrile, acetone and water, and then air dried. This procedure is an adoption of that described by Wheals, J. of Chromat., 107, 402 (1975) used for bonding of polar stationary phases to microparticulate silica for use in liquid chromatography.

The polyacrylic acid coated derivative is then treated with thionyl chloride to form the polyacid chloride derivative which is reacted with sodium azide to form the polyazide, essentially as previously described, a procedure adapted from that described by Wharton, et al., European J. Biochem., 6, 565 (1968) for attaching bromelin to carboxymethyl cellulose. The antibody, salt precipitated from 0.1 ml of serum and previously incubated with cold antigen, is dissolved in 9.5 ml of water and rapidly added to 0.3 gm of stirred polyazide coated product in five ml of water. This is immediately followed by the addition of 4.5 ml of 0.1 M borate buffer (pH 8.7). The mixture is rotated for one hour at 4° C and then filtered, washed with water, 1.0 M NaCl solution, 0.5 M NaHCO$_3$ solution and the final rinse solution described previously.

Three separate sets of data in the format already presented, from standards using three separately prepared immunoabsorbents, as above described, using the procedures previously described are set forth in Tables 2A, 2B, and 2C.

TABLE 2A

| | Testosterone Antibody and Standards | | | | | | | | |
|---|---|---|---|---|---|---|---|---|---|
| Run | 0* | .125 | .25 | .5 | 1 | 2 | 4 | 8 | 16 |
| 1 | 58.9** | 55.0 | 52.5 | 46.2 | 40.3 | 33.4 | 27.0 | 21.9 | 17.3 |
| 2 | 57.3 | 55.5 | 52.9 | 47.4 | 41.3 | 34.9 | 27.3 | 22.8 | 17.8 |
| 3 | 57.6 | 56.0 | 52.2 | 47.7 | 41.2 | 34.6 | 28.7 | 23.7 | 18.5 |
| 4 | 58.4 | 56.2 | 51.6 | 47.7 | 40.1 | 34.4 | 28.3 | 22.9 | 17.5 |
| Mean | 58.05 | 55.68 | 52.30 | 47.25 | 40.72 | 34.42 | 27.82 | 22.82 | 17.78 |
| SD*** | 0.73 | 0.54 | 0.55 | 0.71 | 0.61 | 0.65 | 0.81 | 0.74 | 0.53 |
| CV**** | 1.26 | 0.97 | 1.05 | 1.51 | 1.51 | 1.89 | 2.90 | 3.23 | 2.95 |

TABLE 2B

| | Estriol Antibody and Standards | | | | | | | |
|---|---|---|---|---|---|---|---|---|
| Run | 0* | .25 | .5 | 1 | 2 | 4 | 8 | 16 |
| 1 | 62.5** | 55.2 | 51.6 | 42.0 | 30.5 | 18.2 | 11.8 | 7.1 |
| 2 | 61.1 | 55.0 | 50.0 | 40.9 | 30.0 | 18.5 | 10.3 | 7.1 |
| 3 | 61.3 | 54.3 | 49.0 | 39.4 | 28.6 | 18.7 | 11.3 | 6.8 |
| 4 | 61.1 | 54.1 | 48.6 | 39.4 | 28.5 | 18.8 | 11.6 | 6.9 |
| 5 | 62.0 | 53.3 | 48.6 | 39.0 | 28.1 | 17.9 | 10.7 | 7.7 |
| Mean | 61.60 | 54.38 | 49.56 | 40.14 | 29.14 | 18.20 | 11.14 | 7.12 |
| SD*** | 0.62 | 0.76 | 1.27 | 1.26 | 1.04 | 0.37 | 0.63 | 0.35 |
| CV**** | 1.01 | 1.39 | 2.57 | 3.15 | 3.58 | 2.00 | 5.62 | 4.90 |

TABLE 2C

| | Progesterone Antibody and Standards | | | | | | | |
|---|---|---|---|---|---|---|---|---|
| Run | 0* | .25 | .5 | 1 | 2 | 4 | 8 | 16 |
| 1 | 58.5** | 55.2 | 56.3 | 49.8 | 43.4 | 33.9 | 23.1 | 16.8 |
| 2 | 57.9 | 56.5 | 53.4 | 49.6 | 42.0 | 32.5 | 22.4 | 16.8 |
| 3 | 58.1 | 56.0 | 52.9 | 48.5 | 42.3 | 32.8 | 23.3 | 15.3 |
| 4 | 57.0 | 56.0 | 52.9 | 48.0 | 41.0 | 31.3 | 23.0 | 15.5 |
| Mean | 57.88 | 55.93 | 53.88 | 48.98 | 42.18 | 32.63 | 22.95 | 16.10 |
| SD*** | 0.63 | 0.54 | 1.64 | 0.87 | 0.99 | 1.07 | 0.39 | 0.81 |

TABLE 2C-continued

| Run | Progesterone Antibody and Standards | | | | | | | |
|---|---|---|---|---|---|---|---|---|
| | 0* | .25 | .5 | 1 | 2 | 4 | 8 | 16 |
| CV**** | 1.10 | 0.96 | 3.03 | 1.77 | 2.34 | 3.28 | 1.69 | 5.05 |

Once a vinyl coated derivative is formed, several variants are possible. In one series, the vinyl coated derivative is reacted with allyl isothiocyanate to form a polyisothiocyanate derivative of the vinyl coated substrate. Another series involves reaction with allyl amine to form a polyallyl amine product from which multiple variants may be made. Treatment with epichlorohydrin produces the polyepoxide derivative of the basic vinyl coated allyl amine derivative substrate, which may be conjugated to an antibody. Treatment of the allyl amine derivative with toluene diisocyanate results in a polyisocyanate derivative linked through the amine, which may then be conjugated; treatment with glutaraldehyde results in a polyaldehyde; while treatment with cyanuric chloride produces a polycyanuric chloride derivative, all of which may be conjugated. It is also possible to treat the allyl amine derivative with succinic anhydride to form the polycarboxyl derivative through an amide linkage which can then be converted to the polyazide by treatment with thionyl chloride and sodium azide, and then conjugated.

Treatment of the allyl amine derivative with thiophosgene results in polyisothiocyanate derivatives which may be reacted either with carboxymethyl cellulose or dextran. The carboxymethyl cellulose product may then be treated to convert the carboxyl groups to azide groups and conjugated, as described, while the dextran product may be treated with toluene dissocyanate to form a polyisocyanate derivative, with epichlorohydrin to form a polyepoxide derivative, with thiophosgene to form a polychlorthioformate, with ethyl chloroformate to form a polycarbonate, and with thiocarbonyl diimidazole to form a polythiocarbonate, all of which may be conjugated. The dextran derivative of the vinyl coated substrate may be reacted with cyanuric chloride to form a polycyanuric chloride derivative which may be conjugated, or with succinic anhydride to form a carboxyl variant of the dextran derivative of the vinyl coated product, which may be converted to an azide by treatment with thionyl chloride and sodium azide as discussed.

A preferred material is a polythiol derivative of the vinyl coated substrate, which is prepared by using one gram of the vinyl coated substrate, prepared as described, 0.48 ml (0.445gm) of allyl mercaptan and 0.6 gm of benzoyl peroxide in 300 ml of acetonitrile and refluxing for two hours while stirring. The product is filtered and Soxhlet extracted, as described to produce a polythiol derivative of a vinyl coated substrate.

Conjugation of antibody through the carboxyl group to the polythiolderivative is carried out by using a water soluble carbodiimide coupling agent. The salt percipitate from 0.1 ml of serum is dissolved in four ml of water and incubated with cold antigen. The solution is added to 300 mg of the polythiol derivative and pH is adjusted to 4.7 with 0.05 M HCl solution. A solution of 150 mg of 1-ethyl-3-(3-dimethylaminopropyl) carbodiimide in 0.3 ml of water is added and the pH again adjusted to 4.7 with 0.05 M HCl solution. The mixture is stirred magnetically at room temperature for one hour while the pH is monitored and maintained at 4.7 by the addition of 0.05 N NaOH solution. Stirring is then continued for 17 hours after which the supernatant is removed and the product rotated for 20 minutes with 10 ml of a 0.02 M iodoacetamide—0.2 M NaHCO$_3$ solution (pH 8.0). The support is then washed five times with 10 ml of 0.1 M NaCl solution and once with 10 ml of the final wash buffer described. The procedure is a variant of that described by Cuatrecasas, J. Biol. Chem., 245, 3059 (1970) for coupling of carboxyl containing ligands to sulfhydrylagarose.

Data in the form already presented, from standards, using the above prepared immunoadsorbent, are as follows:

TABLE 3

| Run | Progesterone Antibody and Standards | | | | | | | |
|---|---|---|---|---|---|---|---|---|
| | 0* | .25 | .5 | 1 | 2 | 4 | 8 | 16 |
| 1 | 45.0** | 42.3 | 39.6 | 35.2 | 29.9 | 24.4 | 21.0 | 18.1 |
| 2 | 43.1 | 40.6 | 38.6 | 34.7 | 29.2 | 24.9 | 20.6 | 17.4 |
| 3 | 41.5 | 39.8 | 36.9 | 33.8 | 27.9 | 24.7 | 20.4 | 17.5 |
| 4 | 41.6 | 39.2 | 36.2 | 33.5 | 28.7 | 24.6 | 19.7 | 16.9 |
| 5 | 40.8 | 38.6 | 36.2 | 31.9 | 28.5 | 24.3 | 20.1 | 17.4 |
| 6 | 39.6 | 37.5 | 36.3 | 32.0 | 28.1 | 25.0 | 17.2 | 15.0 |
| Mean | 41.93 | 39.67 | 37.30 | 33.52 | 28.72 | 24.65 | 19.83 | 17.05 |
| SD*** | 1.89 | 1.67 | 1.45 | 1.36 | .74 | .27 | 1.36 | 1.07 |
| CV**** | 4.50 | 4.20 | 3.90 | 4.05 | 2.57 | 1.11 | 6.88 | 6.30 |

The vinyl coated substrate may be reacted with any one of hydroxypropylacrylate, hydroxyethylmethacrylate or hydroxyethylacrylate, each of which may be reacted with cyanuric chloride to form a polycyanuric chloride derivative which may be conjugated.

By another procedure, the vinyl coated substrate may be reacted with acrylamide from which still another series of products, all polyamide derivatives may be made. For example, the acrylamide derivative may be reacted with polyethylene imine to form an imine derivative which may be reacted with glutaraldehyde to form a polyaldehyde derivative which may be conjugated. An amine derivative may be formed by reaction with ethylenediamine and reacted with glutaraldehyde to form a polyaldehyde derivative, with thiophosgene to form a polyisothiocyanate derivative, or with cyanuric chloride, each of which may be conjugated. Where hexamethylenediamine is reacted with the acrylamide, the product may be reacted with glutaraldehyde to form a polyaldehyde derivative.

A preferred material is that formed from the vinyl coated product by reaction with acrylamide and conversion to the polyhydrazide which is reacted to form the polyacyl azide which is then conjugated. The polyamide derivative is formed by refluxing 10.5 gm of the vinyl coated material with 4.44 gm of acrylamide and 0.43 gm of benzoyl peroxide in 1050 ml of acetonitrile, as described. To 5.0 gm of the resulting polyacrylamide coated product suspended in 5 ml of water, 25 ml of 6 M hydrazine hydrate is added and the mixture stirred in a 50° C water bath for seven hours. The product is then filtered, washed with 0.1 M NaCl solution until the filtrate is yellow and tested with 2,4,6-trinitrobenzenesulfonate.

A 1.1 gram sample of the product, the polyhydrazide derivative, is treated at 4° C for 45 minutes with a mixture of 150 ml of 0.3 M HCl solution and 10 ml of 1.0 M NaNo$_2$ solution. The product, a polyacyl azide derivative, is then filtered, washed with 0.3 M HCl solution, 0.1 M sulfamic acid solution and water. In the conjugation sequence, the salt precipitate from 0.1 ml of serum is dissolved in 0.8 ml of 0.1 M sodium borate buffer and after incubation with cold antigen, is rotated for four days at 4° C with the polyacyl azide coated product.

The conjugation product is then washed twice with 10 ml of 0.2 M NaCl solution, twice with 10 ml of water and once with 10 ml of the final wash buffer previously described.

The procedure for forming the polyhydrazide, the polyacylazide and the conjugation sequence are variants of the procedure described by Inmann et al, Biochem. 8, 4047 (1969) for the coupling of various primary aliphatic amines and bovine serum albumen to cross-linked polyacrylamide beads.

Data in the form already presented, from standards, using the above prepared immunoadsorbent, are as follows:

TABLE 4

| Run | Progesterone Antibody and Standards | | | | | | | |
|---|---|---|---|---|---|---|---|---|
|  | 0* | .25 | .5 | 1 | 2 | 4 | 8 | 16 |
| 1 | 58.6** | 56.5 | 56.3 | 52.8 | 47.8 | 40.1 | 32.3 | 25.5 |
| 2 | 57.8 | 57.1 | 55.4 | 52.0 | 49.4 | 40.3 | 32.7 | 24.5 |
| 3 | 59.1 | 57.0 | 56.8 | 52.1 | 47.4 | 40.1 | 34.0 | 25.6 |
| 4 | 58.4 | 58.3 | 55.9 | 52.1 | 47.2 | 39.5 | 32.3 | 24.9 |
| 5 | 61.6 | 59.6 | 57.1 | 53.4 | 48.6 | 42.2 | 33.3 | 26.5 |
| Mean | 59.10 | 57.70 | 56.30 | 52.48 | 48.08 | 40.44 | 32.92 | 25.40 |
| SD*** | 1.47 | 1.25 | .68 | .61 | .91 | 1.03 | .73 | .76 |
| CV**** | 2.49 | 2.17 | 1.21 | 1.16 | 1.89 | 2.55 | 2.22 | 2.99 |

The acrylamide derivative of the vinyl coated product may also be treated with lead tetraacetate to form a polyisocyanate derivative, which may also be used in another series. For example, the formed isocyanate derivative may be reacted with dextran which may then be activated by treatment with epichlorohydrin to form a polyepoxide, or activated by reaction with toluene diisocyanate to form a polyisocyanate derivative, each of which may be conjugated. Alternatively, the formed dextran derivative may be reacted with succinic anhydride to form a polycarboxyl derivative which is then converted to a polyacyl azide by thionyl chloride and sodium azide to provide a product which may be conjugated. Still another alternative is the formation of polyisocyanate by reacting the acrylamide derivative with lead tetraacetate, followed by reaction with carboxymethyl cellulose to form a polycarboxyl derivative which is then converted to a polyacyl azide which may be conjugated.

Another preferred form of the immunoadsorbent is a polyacyl azide formed from the vinyl coated product by reaction with allyl alcohol. In this sequence, 15 grams of the vinyl coated material, prepared as described, 6.0 ml (5.11 grams) of allyl alcohol, 0.6 grams of benzoyl peroxide and 1500 ml of acetonitrile are mechanically stirred at room temperature for 18 to 24 hours rather than refluxing. The product, a polyallyl alcohol derivative is then converted to a polycarboxyl form by reacting 1.23 grams of the polyallyl alcohol derivative with 1.148 gm of succinic anhydride in 100 ml of dried distilled pyridine. The mixture is heated at 53° – 57° C for 16-24 hours, cooled, filtered, and washed with 100 ml each of 0.05 M HCl solution, 0.1 M HCl solution, water and acetone. The polycarboxyl derivative is then treated with thionyl chloride to form the polyacid chloride which is then treated with sodium azide to form the polyacyl azide and conjugated, all as already described.

Data in the form already presented, from standards, using the above prepared immunoadsorbent, are as follows:

TABLE 5

| Run | Progesterone Antibody and Standards | | | | | | | |
|---|---|---|---|---|---|---|---|---|
|  | 0* | .25 | .5 | 1 | 2 | 4 | 8 | 16 |
| 1 | 57.1** | 56.5 | 49.1 | 42.9 | 36.1 | 28.4 | 22.5 | 18.2 |
| 2 | 56.3 | 52.3 | 47.8 | 42.9 | 35.0 | 27.1 | 21.5 | 17.1 |
| 3 | 56.4 | 51.4 | 47.9 | 42.9 | 35.5 | 28.6 | 21.6 | 18.0 |
| 4 | 55.9 | 51.4 | 47.6 | 41.6 | 35.0 | 27.6 | 21.3 | 17.6 |
| 5 | 55.2 | 50.6 | 46.9 | 41.2 | 34.5 | 27.6 | 21.5 | 17.8 |
| 6 | 54.3 | 49.9 | 46.8 | 41.4 | 33.9 | 27.4 | 21.7 | 17.2 |
| Mean | 55.87 | 51.32 | 47.68 | 42.15 | 35.00 | 27.78 | 21.68 | 17.65 |
| SD*** | .99 | .95 | .83 | .83 | .76 | .59 | .42 | .44 |
| CV**** | 1.77 | 1.85 | 1.74 | 1.97 | 2.17 | 2.12 | 1.94 | 2.49 |

As variants, the polyallylalcohol derivative may be reacted with epichlorohydrin to form a polyepoxide derivative, or with toluene diisocyanate to form a polyisocyanate derivative, each of which may be conjugated. Alternatively, the polyallylalcohol derivative may be reacted with cyanuric chloride which may then be reacted with dextran or carboxymethyl cellulose to form a polyhydroxy derivative and a polycarboxyl derivative, respectively. The dextran derivative may then be activated by treatment with cyanogen bromide (see Ser. No. 565,848) to form a polyimidocarbonate derivative, by treatment with epichlorohydrin to form a polyepoxide derivative, or by toluene diisocyanate to form a polyisocyanate derivative, each of which may then be conjugated. The polycarboxyl derivative may be converted to a polyacyl azide derivative by treatment with thionyl chloride and sodium azide, and conjugated.

The barrier material is water insoluble when attached to the substrate. Thus, for example, the preferred dextran is a material having a molecular weight of 70,000 although other materials may be used and activated as here described.

The data above given for the standards used progesterone estriol, and testosterone as the standards, as illustrative of typical antigens which may be assayed by this procedure. It is understood, however, that the antigen may be any of the previously mentioned materials, and that a preincubation sequence may be employed as described in Ser. No. 774,390, filed of even date herewith. It will also be understood that the binding activity of the immunoadsorbent is sufficient to provide reliable data and although fixed for each immunoadsorbent, may vary widely. It may be sufficiently high to bind 80% or more of anticipated antigen concentration in any series of samples and is thus useable in the preincubation sequence above described.

From the above, it will be apparent that the preferred forms of immunoadsorbent are those described by the specific examples in which data were presented. These products operate as well as or better then the products described in Ser. No. 565,848 in a radioimmunoassay procedure in which the immunoadsorbent is reused for continued assays of the same antigen through a stoichiometric release of the antigen bound to the antibodies conjugated on the substrate, prepared as described. In a flow-through system both the flow qualities and stability of the reusable immunoadsorbent are important for reliable results over an extended period of time.

By the present invention a substantially improved procedure for radioimmunoassay is provided through the use of a novel and improved immobilized immunoadsorbent capable of long useage with reliability and repeatability. In effect, the immunoadsorbent includes a substrate to which the functional groups are attached, the substrate in turn being composed of particulate solids each of which is a solid core with a porous crust. Reached to the crust is a barrier, in the sense that reactive sites which tend to bind antigen are masked. The barrier may be a single barrier such as dextran, polyolefins, cellulose or carboxymethyl cellulose, for example, or a composite barrier of polyolefin and any one of dextran, cellulose, and carboxymethyl cellulose. The barrier is activated, by the reactions disclosed, to provide functional groups to which the antibody may be conjugated.

The solid nature of particles forming the nucleus of the substrate operates to assure proper packing and thus proper flow when material is flowed through the immunoadsorbent. The barrier coating assures stability and activity while the conjugation, in the regime described, assures both proper binding of the antibody and release of the antigen.

It will be apparent to those skilled in the art that the improved radioimmunoassay procedure of this invention is achieved by use of an improved immunoadsorbent and that various modifications may be made with respect to the subject matter herein disclosed. For example, a barrier or composite barrier may be used with other substrates where activity of the substrate presents potential problems. Other modifications, changes and alterations will be apparent from the foregoing description without departing from the scope of the invention as set forth in the appended claims.

I claim:

1. In a method of radioimmunoassay wherein an antigen bearing sample and a radioactive labelled antigen are brought into contact with an immobilized immunoadsorbent to form a fraction bound to the immunoadsorbent and an unbound fraction and wherein the concentration of the antigen is determined as a function of the bound or unbound fraction, or both, the improvement comprising:

flowing an antigen bearing sample and a radioactive labelled antigen into contact with an immunoadsorbent comprised of a solid particulate substrate having covalently bound thereto antibodies specific to the antigen to form a bound and unbound fraction, said antibody including carboxyl and amine functional groups, said substrate including a barrier coating having attached thereto functional groups selected from the group consisting of acyl azide, chlorothioformate, epoxide, carbonate, thiocarbonate, isocyanate, cyanuric chloride, polyazide, polychlorothioformate, polyepoxide, polycarbonate, polythiocarbonate, polyisocyanate, polycyanuric chloride, polyimidocarbonate, polyaldehyde and polythiol, said antibody being conjugated to said substrate by reaction between one of said carboxyl and amine groups with one of said functional groups attached to said substrate through said barrier coating, regenerating the immunoadsorbent by releasing substantially all of the antigens bound to the immunoadsorbent by rinsing said immunoadsorbent with an eluting solvent, detecting the labelled antigen in at least one or both of the unbound fraction and the bound fraction released by said eluting solvent, and reusing the immunoadsorbent for further assays of further samples containing the antigen to which said antibodies are specific.

2. A method as set forth in claim 1 wherein said solid particulate substrate includes a particulate material composed of impervious glass spheres coated with an outer porous crust of microspheres.

3. A method as set forth in claim 1 wherein said particulate substrate includes a mass of porous refractory particles, and said barrier coating being a water insoluble material chemically bonded to said particles.

4. A method as set forth in claim 3 wherein said group is an azide and said barrier coating is dextran.

5. A method as set forth in claim 3 wherein said barrier coating is a polyolefin material and said functional group is a polyacyl azide.

6. A method as set forth in claim 3 wherein said barrier coating is a polyolefin material and said functional group is a polythiol.

7. A method as set forth in claim 3 wherein said barrier coating is a combination of a polyolefin material and a material selected from the group consisting of dextran, cellulose and carboxymethyl cellulose.

8. A method as set forth in claim 1 wherein said sample is preincubated with said antigen prior to flow through said immunoadsorbent.

9. A method as set forth in claim 1 wherein said substrate includes solid particulate material composed of impervious glass spheres each coated with an outer porous crust of microspheres, said spheres being of a diameter of between 5 and 500 microns, and said microspheres being of a diameter of between 5 millimicrons and 1 micron.

10. A method as set forth in claim 1 wherein said particulate substrate has a surface area of between 0.8 and 1.0 $m^2$/gram.

11. A method as set forth in claim 1 wherein the activity of the immunoadsorbent is not less than 80% of the concentration of the antigen in the sample.

12. A method of forming an immobilized immunoadsorbent for use in radioimmunoassay comprising:

providing a particulate solid material having a porous surface and a barrier coating on said particulate solid, activating said barrier coating to attach thereto chemically a material having a functional group selected from the group consisting of acyl azide, chlorothioformate, epoxide, carbonate, thiocarbonate, isocyanate, cyanuric chloride, polyacyl azide, polychlorothioformate, polyepoxide, polycarbonate, polythiocarbonate, polyisocyanate, polycyanuric chloride, polyimidocarbonate, polyaldehyde and polythiol, and conjugating to said barrier coated substrate an antibody specific to an antigen by covalently coupling through said groups to the carboxyl or amine group of said antibody.

13. A method as set forth in claim 12 wherein said barrier coating is selected from the group consisting of polyolefin, dextran, carboxymethyl cellulose and cellulose, and combinations thereof.

14. A method as set forth in claim 12 wherein said functional group is an acyl azide.

15. A method as set forth in claim 12 wherein said functional group is a polyacyl azide.

16. A method as set forth in claim 12 wherein said functional group is a polythiol.

17. An immobilized immunoadsorbent for use in radioimmunoassay comprising:

a solid particulate substrate having covalently bound thereto antibodies specific to an antigen, said antibody including carboxyl and amine functional groups, said substrate including a barrier coating having attached thereto functional groups selected from the group consisting of acyl azide, chlorothioformate, epoxide, carbonate, thiocarbonate, isocyanate, cyanuric chloride, polyacyl azide, polychlorothioformate, polyepoxide, polycarbonate, polythiocarbonate, polyisocyanate, polycyanuric chloride, polyimidocarbonate, polyaldehyde and polythiol, and said antibody being conjugated to said substrate by reaction between one of said carboxyl and amine groups with one of said functional groups attached to said substrate through said barrier coating.

* * * * *